US012599333B2

(12) United States Patent
Shultz et al.

(10) Patent No.: US 12,599,333 B2
(45) Date of Patent: Apr. 14, 2026

(54) MULTI-AXIAL JOINT LAXITY TESTING APPARATUS AND METHOD

(71) Applicant: University of North Carolina at Greensboro, Greensboro, NC (US)

(72) Inventors: Sandra Janine Shultz, Greensboro, NC (US); Randy Joe Schmitz, Oak Ridge, NC (US); James Avery Coppock, Durham, NC (US); Sam Seyedin, Greensboro, NC (US)

(73) Assignee: University of North Carolina at Greensboro, Greensboro, NC (US)

( * ) Notice: Subject to any disclaimer, the term of this patent is extended or adjusted under 35 U.S.C. 154(b) by 1297 days.

(21) Appl. No.: 17/238,786

(22) Filed: Apr. 23, 2021

(65) Prior Publication Data

US 2021/0251566 A1     Aug. 19, 2021

Related U.S. Application Data

(63) Continuation of application No. PCT/US2019/059648, filed on Nov. 4, 2019.
(Continued)

(51) Int. Cl.
*A61B 5/00* (2006.01)
*A61B 5/11* (2006.01)

(52) U.S. Cl.
CPC .......... *A61B 5/4585* (2013.01); *A61B 5/0048* (2013.01); *A61B 5/1121* (2013.01);
(Continued)

(58) Field of Classification Search
None
See application file for complete search history.

(56) References Cited

U.S. PATENT DOCUMENTS

2009/0124936 A1     5/2009   Branch et al.
2012/0046540 A1     2/2012   Branch et al.
(Continued)

FOREIGN PATENT DOCUMENTS

WO         2014028288 A1     2/2014

OTHER PUBLICATIONS

ISA/EP; International Search Report and Written Opinion for International Patent Application No. PCT/US19/59648 dated Apr. 8, 2020, 13 pages.
(Continued)

*Primary Examiner* — Benjamin S Melhus
(74) *Attorney, Agent, or Firm* — NK Patent Law

(57) ABSTRACT

Knee joint laxity testing apparatus includes a thigh cradle assembly, a shank cradle assembly, and a heel cradle assembly. The apparatus is configured to measure knee laxity in three planes of motion: anterior-posterior translations; varus-valgus rotations; and internal-external rotations. The thigh cradle assembly, shank cradle assembly, and heel cradle assembly are mounted on a common base. A thigh fixation system is attached to the thigh cradle assembly both at the proximal and distal ends to firmly stabilize the thigh in the thigh cradle. The patella pad and distal thigh fixation system are mounted on a U-bar assembly. The distal thigh fixation system includes two condyle pad adjustment arms upon which a respective condyle pad is mounted, and a patella pad mounted to a linear track on an underside of the U-bar assembly.

31 Claims, 5 Drawing Sheets

Related U.S. Application Data

(60) Provisional application No. 62/755,817, filed on Nov. 5, 2018.

(52) U.S. Cl.
CPC .......... *A61B 5/6828* (2013.01); *A61B 5/6829* (2013.01); *A61B 5/742* (2013.01); *A61B 2560/0487* (2013.01); *A61B 2562/0252* (2013.01)

(56) References Cited

U.S. PATENT DOCUMENTS

| | | |
|---|---|---|
| 2013/0204119 A1 | 8/2013 | Coelho Do Sameiro Espregue Mendes |
| 2017/0143250 A1* | 5/2017 | Branch .................... A61B 5/11 |

OTHER PUBLICATIONS

WIPO; International Preliminary Report on Patentability for International Patent Application No. PCT/US19/59648 dated May 20, 2021, 10 pages.

Shultz, Sandra, et al., "Identifying Multiplanar Knee Laxity Profiles and Associated Physical Characteristics", Journal of Athletic Training, vol. 47, No. 2, Mar. 2012, 21 pages.

* cited by examiner

MULTI-AXIAL JOINT LAXITY TESTING APPARATUS AND METHOD

CROSS-REFERENCE TO RELATED APPLICATIONS

This application is a continuation of International Patent Application No. PCT/US2019/059648 filed on Nov. 4, 2019, which claims priority to U.S. Provisional Patent Application No. 62/755,817 filed on Nov. 5, 2018, the entire contents of which are incorporated by reference herein.

TECHNICAL FIELD

The present disclosure relates to human joint testing, and particularly, to devices and methods for multi-axial joint laxity testing.

BACKGROUND

Prior devices for joint laxity measurement are expensive, take considerable training, take considerable time to gain accurate measurements, and still can lack reliability and agreement of measures between testers. Prior devices that do exist, only measure AP laxity, or Internal-External rotation laxity. The need for knee laxity measuring equipment has increased in recent years, given two prospective studies that have independently determined that knee laxity is a strong predictor of ACL (anterior cruciate ligament) injury risk. Publications on knee laxity demonstrate clear sex-based differences in laxity, changes that can occur during the menstrual cycle and during exercise, and the biomechanical consequences of these changes. Moreover, there are many clinical benefits to be had from the assessment of frontal plane knee laxity for screening and diagnostic purposes; however, there is no specific device available for this purpose apart from X-ray examination. Commercial laxity assessment devices (arthrometers) available in the market suffer from inconsistent and difficult measurements which has contributed to poor adoption of these devices by clinicians.

There is accordingly a need for a device that is easily accessible and can be efficiently used by clinicians and other end users for mass screening purposes that can accurately identify those with increased laxity and screen for those at risk.

SUMMARY

This summary is provided to introduce in a simplified form concepts that are further described in the following detailed descriptions. This summary is not intended to identify key features or essential features of the claimed subject matter, nor is it to be construed as limiting the scope of the claimed subject matter.

Disclosed herein is a method of a knee joint laxity testing apparatus. According to various embodiments, the apparatus comprises a thigh cradle assembly; a shank cradle assembly; and a heel cradle assembly. The apparatus is configured to measure knee laxity in three planes of motion.

According to one or more embodiments, the three planes of motion comprise anterior-posterior translations; varus-valgus rotations; and internal-external rotations.

According to one or more embodiments, the apparatus further comprises a base upon which the thigh cradle assembly, shank cradle assembly, and heel cradle assembly are mounted.

According to one or more embodiments, the apparatus further comprises a patella, a thigh fixation system positioned between the thigh cradle assembly and shank cradle assembly, and at least two clamping arms coupled to the thigh cradle assembly for securing a thigh positioned on the thigh cradle assembly.

According to one or more embodiments, the apparatus further comprises a U-bar assembly upon which the patella pad and a distal thigh fixation system is mounted.

According to one or more embodiments, the distal thigh fixation system comprises two condyle pads attached to and guided by a respective condyle pad adjustment arm.

According to one or more embodiments, the condyle pads extend from, and are adjustable relative to, the U-bar assembly.

According to one or more embodiments, the thigh fixation system further comprises a patella pad mounted to a linear track on an underside of the U-bar assembly.

According to one or more embodiments, the U-bar assembly comprises a U-bar adjustably mounted upon vertical height adjustment bars.

According to one or more embodiments, the patella pad interfaces with a patella region of the knee of a patient.

According to one or more embodiments, the patella pad has a cushioned, deformable, and/or resilient surface which interfaces with the patella region of the knee of a patient to increase comfort and conformity to varying patellar shapes.

According to one or more embodiments, the shank cradle assembly comprises an actuated linear mechanism for providing an anterior-posterior (AP) loading.

According to one or more embodiments, the heel cradle assembly further comprises an IE rotational fixture mounted on a carriage, and a heel cradle mounted on the IE rotational fixture.

According to one or more embodiments, the IE rotational fixture is mounted on the carriage via a linear track to facilitate varus-vargus laxity testing. The linear track also allows the heel cradle to move in varus-valgus direction.

According to one or more embodiments, the heel cradle is mounted on the IE rotational fixture via a rotary shaft.

Disclosed herein is a system for knee joint laxity testing. According to one or more embodiments, the system comprises: a knee joint laxity testing apparatus engaged with a person's knee, the knee joint laxity testing apparatus comprising a thigh cradle assembly, a shank cradle assembly, and a heel cradle assembly, the knee joint laxity testing apparatus configured to measure knee laxity values in three planes of motion. A controller is coupled to the knee joint laxity testing apparatus, the controller configured to receive the measured knee laxity values in three planes of motion. An application is configured to display, on a user interface of a computing device, the measured knee laxity values in three planes of motion.

According to one or more embodiments, the computing device comprises a processor communicably coupled to at least one memory; and program instructions which when executed by the processor cause the processor to: receive, from the controller, the measured knee laxity values in three planes of motion; and, display, on the user interface of the computing device, a level of deviation of a measured knee laxity value from a predetermined value.

According to one or more embodiments, the controller is in communication with at least one motor configured to perform one of: the anterior-posterior translations; the varus-valgus rotations; and the internal-external rotations.

According to one or more embodiments, the controller is in communication with at least one sensor configured to sense one or more of a force and a displacement resulting from one of: the anterior-posterior translations; the varus-valgus rotations; and the internal-external rotations.

According to one or more embodiments, the system further comprises a base upon which the thigh cradle assembly, shank cradle assembly, and heel cradle assembly are mounted.

According to one or more embodiments, the system further comprises proximal thigh clamps for securing a thigh positioned on the thigh cradle assembly.

According to one or more embodiments, the system further comprises a patella, a thigh fixation system positioned between the thigh cradle assembly and shank cradle assembly, and at least two clamping arms coupled to the thigh cradle assembly for securing a thigh positioned on the thigh cradle assembly.

According to one or more embodiments, the system further comprises a U-bar assembly upon which the patella pad and distal thigh fixation system is mounted.

According to one or more embodiments, the distal thigh fixation system comprises two condyle pads attached to and guided by a respective condyle pad adjustment arm.

According to one or more embodiments, the condyle pads extend from and are adjustable relative to the U-bar assembly.

According to one or more embodiments, the thigh fixation system further comprises a patella pad mounted to a linear track on an underside of the U-bar assembly.

According to one or more embodiments, the U-bar assembly comprises a U-bar adjustably mounted upon vertical height adjustment bars.

According to one or more embodiments, the IE rotational fixture is mounted on the carriage via a linear track to facilitate varus-vargus laxity testing. The linear track allows the heel cradle to move in varus-valgus direction.

According to one or more embodiments, the thigh fixation system comprises a patella pad mounted to the linear track on the underside of the U-bar assembly, and wherein the patella pad interfaces with a patella region of the knee of a patient.

According to one or more embodiments, the patella pad has a cushioned, deformable, and/or resilient surface which interfaces with the patella region of the knee of a patient to increase comfort and conformity to varying patellar shapes.

Disclosed herein is a method for measure knee laxity with a knee joint laxity testing apparatus According to one or more embodiments, the method comprises: measuring knee laxity values in three planes of motion with a knee joint laxity testing apparatus engaged with a person's knee, wherein the knee joint laxity testing apparatus comprises a thigh cradle assembly, a shank cradle assembly, and a heel cradle assembly, receiving at a controller coupled to the knee joint laxity testing apparatus the measured knee laxity values; and, displaying, on a user interface of a computing device, the measured knee laxity values.

According to one or more embodiments, the method further comprises receiving, from the controller, the measured knee laxity values in three planes of motion; and, displaying, on the user interface of a computing device, a level of deviation of a measured knee laxity value from a predetermined value.

According to one or more embodiments, the method further comprises the controller communicating with at least one motor performing one of: the anterior-posterior translations; the varus-valgus rotations; and the internal-external rotations.

According to one or more embodiments, the method further comprises the controller communicating with at least one sensor configured to sense one or more of a force and a displacement resulting one of: the anterior-posterior translations; the varus-valgus rotations; and the internal-external rotations.

DETAILED DESCRIPTION

Figure 1:
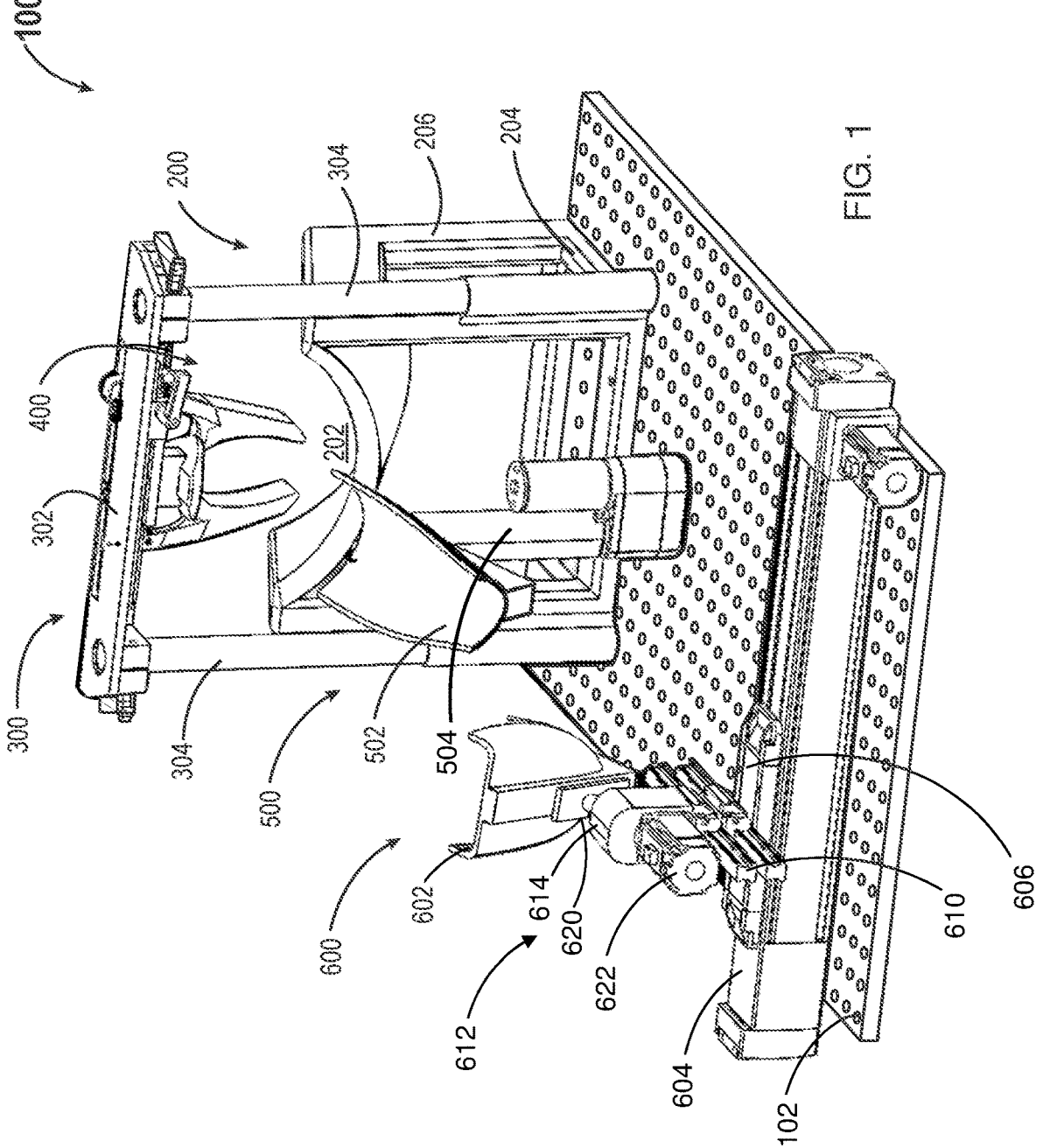
FIG. 1 is a perspective view of a multi-axial joint laxity testing apparatus, according to at least one embodiment.

The following description and drawings are illustrative and are not to be construed as limiting. Numerous specific details are described to provide a thorough understanding of the disclosure. However, in certain instances, well-known or conventional details are not described in order to avoid obscuring the description. Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and is not intended to further limit the scope and meaning of the disclosure or of any exemplified term. Likewise, the disclosure is not limited to various embodiments given in this specification. For example, some embodiments can be partially or fully automated whereas other embodiments may be set up for 100% manual operations.

Like reference numbers used throughout the drawings depict like or similar elements. Unless described or implied as exclusive alternatives, features throughout the drawings and descriptions should be taken as cumulative, such that features expressly associated with some particular embodiments can be combined with other embodiments.

Without intent to limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

As used herein, the term "end user" includes healthcare professionals and researchers who assess knee joint health, treat, and rehabilitate knee injuries that include but are not limited to, physicians, physical therapists, orthopedic specialists, orthotists and athletic trainers.

According to various embodiments of the presently disclosed subject matter, a novel instrumented knee ligament/ laxity testing apparatus as disclosed herein provides for conducting laxity tests to obtain objective measures of knee joint rotational displacement in the frontal (VV, varus-valgus laxity) plane, transverse (IE, internal-external rotation knee laxity) plane, and translational displacement in the sagittal (AP, anterior-posterior knee laxity) plane. Laxity is operationally defined as the translational or rotational displacement of the tibia relative to the femur under an applied load. AP laxity tests the isolated integrity of the anterior (ACL) and posterior (PCL) cruciate ligaments. VV laxity tests the isolated integrity of the medial and lateral collateral ligaments. IE laxity tests the integrity of the both cruciate and collateral ligaments.

In various embodiments, the subject matter as disclosed herein can advantageously provide for the ability to quickly, accurately and reliably perform objective assessments of knee laxity in three planes of motion. Embodiments as disclosed herein can advantageously amplify and augment the subjective abilities of end users.

In some embodiments, the novel instrumented knee ligament/laxity testing apparatus as described herein is automated and can include a system such as system 700 comprising hardware, software and an automated patient interface for conducting the laxity tests as described herein. Embodiments as disclosed herein can accordingly allow for automated knee assessment methods that could address the limitations of commercially available devices. In at least one embodiment, a robotic medical device is provided that is configured to emulating assessments of knee joint laxity that is otherwise subjectively made by end users having substantial training in the field, for example. Accordingly, while some embodiments can be partially or fully automated, other embodiments may be set up for 100% manual operations.

Laxity is an important measurement because it assists in the diagnosis of ligament injury and joint integrity. Laxity is defined as "the amount a joint deviates from its initial position when a force is applied to it." The deviation is largely restrained by the stabilizing ligaments. Laxity assessments inform an end user such as, for example, a clinician regarding an intervention plan that can avoid injury or that can support a patient's recovery from injury. In practice, end users including healthcare professionals use their hands to move a patient's knee joint for a subjective assessment of laxity (i.e. motion palpation (MP)), thus assessing ligament integrity. During testing for ligament integrity, end users such as clinicians are most commonly subjectively assessing displacement of the joint during passive motion (excursion), and the degree of tissue resistance at the end of the joint range of motion (end feel). Common assessments made by hand in practice often fail to provide a reliably objective metric of knee laxity. By contrast, the measurements made by the embodiments as disclosed herein are designed to emulate some of the hand-made assessments but in a more automated, objective and reproducible fashion. The embodiments as disclosed herein are designed to advantageously conduct three tests to assess laxity in three plans of motion: the anterior-posterior laxity, the varus-valgus rotational laxity and the interior-exterior rotational laxity.

Anterior-posterior knee laxity (APKL) test measures the displacement of the knee joint as force is applied from the posterior side of the joint toward the anterior side of the joint (and visa-versa) when angle between the thigh and the tibia is fixed at an angle of approximately 25-30 degrees. During this test, both the force applied to the knee joint, and the resulting displacement of the knee joint are measured, displayed and recorded. The loci of the force-displacement curves provide diagnostic information, including the "end feel" as the resistance to force applied increases, reducing movement and forming a "plateau" of displacement. Embodiments as disclosed herein can take measurements somewhat similar to a manual Lachman assessment.

Varus-valgus rotational laxity (VVRL) relates to valgus deflection and varus deflection. Valgus deflection first occurs as force is applied against the interior (medial), shank (tibia) causing the distal segment of the joint to pivot more laterally. Conversely, varus deflection occurs as force is applied to the exterior (lateral) side of the shank, resulting in medial deflection of the distal segment of the knee joint. As in anterior-posterior testing, this test is done while the thigh and shank are fixed at an angle of from 0-30 degrees. During this test, both the force applied to the knee joint, and the resulting displacement of the knee joint are measured, displayed and recorded. The loci of the force-displacement curves provide diagnostic information, including the "end feel" as the resistance to force applied increases, reducing movement and forming a "plateau" of displacement. Embodiments as disclosed herein can take measurements somewhat similar to the manual valgus-varus stress test.

Interior-exterior rotational laxity (EIRL) test corresponds to the displacement of the knee joint as the tibia is rotated along its long axis (through the tibia) first toward the exterior (lateral) side of the joint and then to the interior (medial) side of the joint when angle between the thigh and the tibia is fixed at an angle from 0-30 degrees. Embodiments as disclosed herein can take measurements somewhat similar to a simple tibia rotation manual assessment.

As used herein, the term "clinical data registry" is a clinical data registry records information about the health status of patients and the health care they receive over varying periods of time. Clinical data registries typically focus on patients who share a common reason for needing health care. As used herein, the term "end feel" relates to the tactile feedback sensed by the clinician when force is applied by hand to displace the knee joint. As the joint displacement reaches its full range, resistance to displacement rapidly occurs and creates end feel.

According to various embodiments, the device/apparatus includes a thigh stabilization element, and a lower leg and foot stabilization element attached to a contiguous base that can allow isolation of laxity testing in each plane of motion (while locked in the other two planes of motion) with a single positioning of the subject/patient. To use the device, an individual can be positioned in the device atop a treatment table, lying supine with the lower extremity positioned in the thigh cradle (stabilized segment), the lower leg and foot positioned in the leg cradle (moveable segment) such that the knee joint is positioned in the desired amount of tibial rotation and knee flexion.

Prior to testing, the leg and thigh are to be stabilized within cradles that conform to or approximately match the contour of the thigh to firmly stabilize the thigh to the thigh cradle, and to the leg and foot to firmly stabilize in the leg cradle so that when the leg cradle moves relative to the thigh cradle, there would be no auxiliary limb movement (i.e. the foot, ankle and leg move as a single segment). Then, the movement in the frontal and transverse plane would be locked so that cyclic anterior-posterior translations of the tibia on the femur could be performed at fix loads between 0-150 N to measure AP laxity. With the subject remaining in the same position with thigh and leg stabilized, the sagittal and transverse planes would be locked so that cyclic frontal plane rotations of the tibia relative to the femur could be measured between 0-10 Nm of varus and valgus rotational torques to measure varus-valgus knee laxity. Finally, with the subject still positioned in the same manner, the frontal plane and sagittal plane can be locked so that transverse plane rotations of the tibia relative to the femur can occur between 0-5 Nm of internal and external rotation torques to measure internal-external rotation knee laxity. AP translations can be applied with anterior-posterior directed loads of the leg cradle relative to the thigh cradle, in parallel to the joint line, with force measured at the proximal tibia and displacement measured by sensors that accurately depict relative bone movement between the proximal tibia and distal femur in the AP plane. In one testing mode, Frontal and Transverse plane knee rotations can be initiated at the base of the leg/foot plate, where IE rotations would occur through the long axis of the tibia, and frontal plane rotations initiated at the distal tibia as the base of the leg cradle is moved into varus/valgus along an array of linear slides at 90 degree angles to maintain true VV rotations; in an alternate testing mode, the Frontal and Transverse plant knee rotations can be initiated at the proximal end of the leg cradle though similar mechanisms.

Accordingly, in various embodiments, displacement activators can be provided. During conventional, manual testing of the knee joint laxity, clinicians use their hands to provide the force for displacement and the resistance of that force to create "end feel" at the boundaries of the knees range of motion. By contrast, system 700 and a device such as apparatus 100 as disclosed herein accomplish displacement using linear tracks that can be actuated either manually or via motors. In at least one embodiment, the motors are controlled by a computer as the computer monitors feedback sensors for force and displacement.

The linear track can advantageously allow the heel cradle to move in varus-valgus direction. It is to be noted that there are two linear tracks-linear track 610 is a vertical track that is parallel with the lower leg that allows the heel cradle to adjust to different lengths of legs. VV track 604 is a horizontal track that allows the shank to move in varus-valgus directions.

As measured using system 700 as disclosed herein, anterior-posterior displacement measures the movement of the patient's knee in the sagittal plane (somewhat like the Lachman test). With the thigh fixed, the anterior-posterior movement of the tibia relative to the femur is measured as force increases from zero to 150 N.

As measured using the system 700 as disclosed herein, lateral (varus-valgus) displacement measures the movement of the patient's knee in the Frontal plane (somewhat like the valgus-varus stress tests). With the thigh securely fixed, the tibia is moved under a medial-lateral directed rotational force about the knee joint, from zero to 10 Nm.

As measured using the system as disclosed herein, internal-external rotational displacement measures the movement of the patient's knee in the transverse plane. With the thigh securely fixed, the tibia is rotated about its long axis under internal-external rotational force of zero to 5 Nm.

In at least one embodiment, a load cell secured at the point at which the force is applied can be configured to record a torque applied based on known force and moment arm distance from the joint. In at least one embodiment, the system is fully automated so that it can cycle through each plane of motion (or isolated motions as desired), without requiring the hands of the end user or clinician (alternately referred to herein as the "tester"), whereby a tester dependent error can inadvertently be introduced. In a further embodiment, in order to reduce the cost of the system and to simplify the size and scope of the system, a manual version is provided whereby the components of the system and/or the knee of the patient/subject can be pushed/pulled along linear tracks to ensure a true planar motion in each direction, thus greatly reducing tester error.

According to various embodiments, conditioning trials at lower (and incrementally increasing loads) can include 3 to 5 test trials. To improve accuracy, it is important that the testing limb be firmly fixed in the device such that movement of the device accurately represents movement of the bones (tibia and femur). Accordingly, in various embodiments, the more proximal thigh clamps and the more distal patellar and condyle clamping systems of the thigh cradle can be designed to tightly "form fit" around the contours of the limb. Accordingly, the system as described herein can include proximal thigh clamps, a distal patella (or patellar) clamping system, and a distal condyle clamping system that operate in conjunction with each other to ensure that the thigh cradle form fits around the contours of the limb. Precision sensors placed on the testing device/apparatus as well as on the limb can operate to cancel out any movement artifact whereby the system and/or the device can accurately measure laxity in all three planes of motion. The system and/or the device can accordingly allow for a quick and easy measurement of tri-planar knee laxity. The system and/or the device can also eliminate the need for an experienced end user or clinician to provide positioning instruction, thus removing as much tester error as possible. The system and/or the device can furthermore provide for objective measures validated against true bony motion which is the gold standard (e.g., x-ray, cadaver testing with bone pins) that can be documented.

Figure 5:
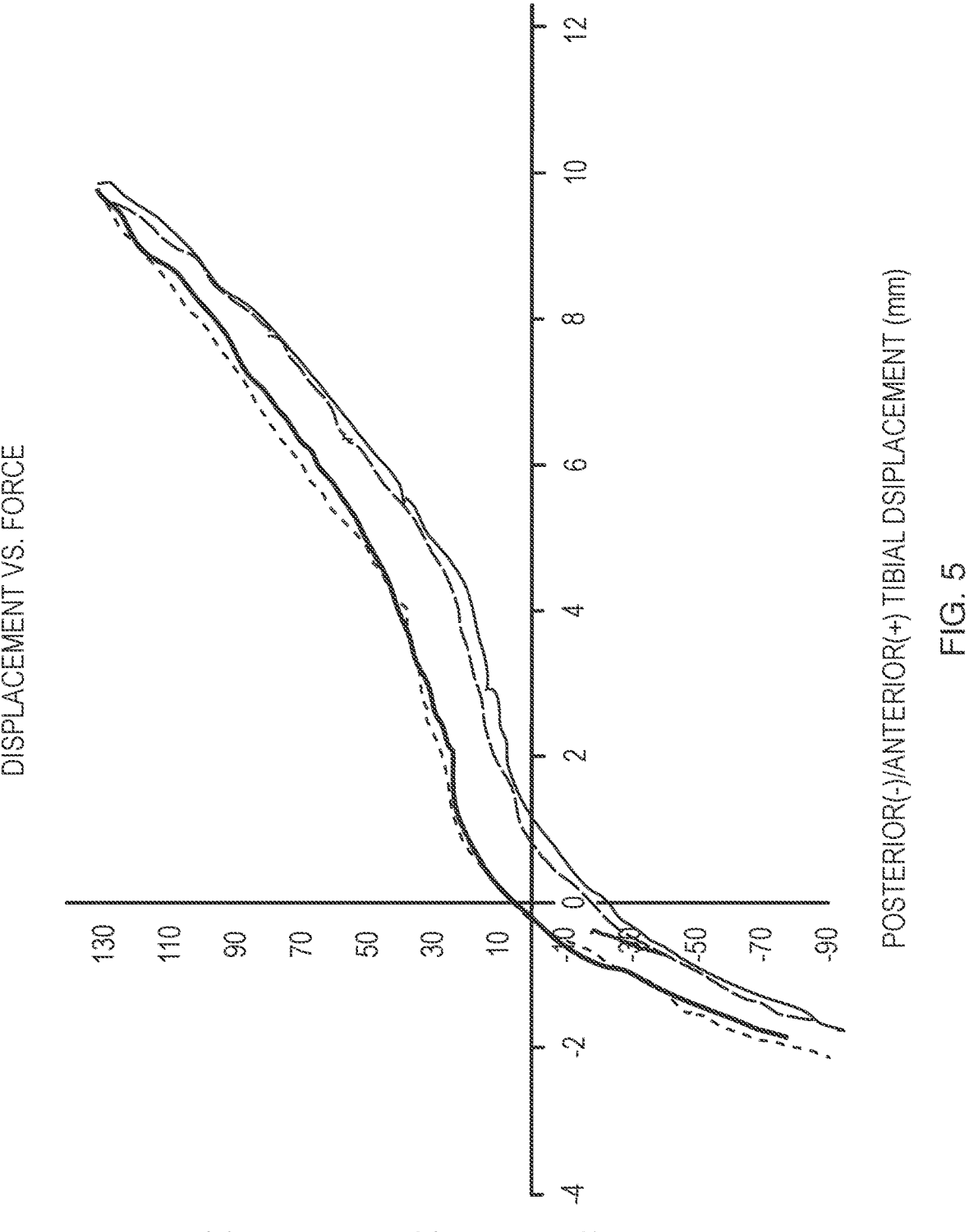
FIG. 5 is a graphical representation of a feedback display illustrating relationship between mechanical displacement and the force applied as measured by multi-axial joint laxity testing apparatus, according to at least one embodiment.

The system/apparatus can include software configured for measuring displacement at a fixed load and constructing a load-displacement curve (for example, as shown in FIG. 5) to quantify joint stiffness/compliance using accompanying software. The software would also calculate relaxation curves, and would allow input of subject height, weight and femur and tibia length so that laxity values can be normalized to body size (this is not a feature of current systems). The thigh and leg cradle may be equipped with a sliding caliper to accurately and efficiency record femur and tibia segment lengths.

A multi-axial joint laxity testing apparatus 100 (may be alternately referred to herein as "apparatus 100" or "apparatus" or "device") according to at least one embodiment is shown in FIG. 1. Apparatus 100 is designed as a portable (tabletop) knee arthrometer for accurate measurement of multi-planar knee joint laxity with minimal time and training required for the technician performing the testing on a subject/patient. Knee joint laxity characterizes the integrity of the cruciate and collateral ligament structures, which play a critical role in maintaining a healthy, stable knee during activities of daily living and sport. As noted earlier, laxity is operationally defined as the translational or rotational displacement of the tibia relative to the femur under an applied load. Instrumented assessment of knee joint laxity has many clinical applications. Specifically, apparatus 100 can be used to screen for knee injury risk potential, to diagnose ligament injuries (in conjunction with clinician and MRI evaluations), to provide evidence of successful repair and healing of surgical repaired of reconstructed ligaments post-surgery and rehabilitation, and to measure progression of joint diseases such as osteoarthritis, and to serve as a prescription for custom knee bracing. With these and related purposes in mind the apparatus 100 is designed with the many novel and advantageous features.

Apparatus 100 measures knee laxity in three planes of motion (AP-anterior-posterior translation; VV-varus-valgus rotations; IER-internal-external rotations of the tibia relative to the femur); current and past commercially available devices only measure AP laxity. This can advantageously be accomplished by measuring VV and IER laxity with a single apparatus in lieu of requiring separate stand-alone devices. The knee moves in three planes of motion, and laxity is not uniform across planes. Inter-planar variations in laxity can be influenced by an individual's sex and anatomy and can impact functional joint health differently depending on the plane(s) of motion where excessive knee joint laxity is most apparent. Thus, apparatus 100 provides a more comprehensive assessment of knee joint laxity in a single device, and with a single positioning of the patient.

Apparatus 100 in some embodiments is fully automated such that it can mechanically load the limb in a reproducible manner, removing human tester error. Tester error accounts for a substantial portion of the total measurement error of current devices. Multiple sources of measurement inconsistency resulting from tester error include hand size and dominance, examiner strength, and the control of rate, direction and magnitude of the applied load. As such, the level of examiner training has a substantial effect on precision and reproducibility of measures. In one embodiment, apparatus 100 does not include automation, i.e., apparatus 100 can be a manual version. Whether apparatus 100 is manual or fully automated, motion in each plane will be guided by a track system, which ensures consistent and repeatable motion in each plane. The manual version can reduce tester error by improved stabilization and positioning of the patient, and by controlling the direction and magnitude of the applied load, thereby rendering the apparatus clinician friendly while simultaneously reducing the level of examiner/tester training that is required. A fully automated apparatus 100 can further remove this source of measurement variation by standardizing the rate of the loading, making the apparatus clinician friendly and accurate in the hands of clinicians of various experience and training. Advantageously, in using the apparatus 100, the patient is stabilized (thigh and foot/ankle) as measurements are acquired. It is to be noted that the linear track system(s) upon which each motion occurs can ensure that the same motion is consistently achieved in each trial and patient.

Apparatus 100 can improve limb stabilization to reduce skin movement artifact associated with soft tissue deformation. Both data from the literature and clinician feedback speak to concerns about inadequate limb stabilization (e.g., stabilization of the thigh, positioning of the lower leg) whereby control of tissue movement artifact is reduced, which contributes to both random and systematic error during laxity test. Apparatus 100 is designed with a thigh stabilization system that can securely fix the thigh during apparatus manipulation of the tibia in all planes of motion. Apparatus 100 further includes a movable shank system that can be customize to each patient's leg to position the tibia relative to the femur in a reproducible and standardized manner for accurate comparison within and between patients and within and between testers. These stabilization mechanisms are intended to increase measurement precision and reproducibility.

Apparatus 100 can be used to measure bone movement as validated against direct imaging. Many laxity devices have not been compared to the gold standard of direct imaging of joint motion (e.g. MRI, radiographs, direct measure of bony motion via cadaver testing). The comparisons performed by the inventors reveal over-estimation of joint motion due to tissue deformation artifact that is not observed by simply comparing one arthrometer to another.

In the embodiment of apparatus 100 illustrated in FIG. 1, the elevated components are, in some form, attached to base 102. This ensures that all components lie on a consistent and definite coordinate system, allowing end users to firmly secure the patient's limb and accurately calculate force and displacement outputs. Base 102, in the illustrated embodiment, provides a contiguous platform that is easily portable to and from a tabletop. This design ensures that measurements can be made based on known distances, reducing measurement error and increasing measurement reliability. Above the base 102, apparatus 100 includes a thigh cradle assembly 200, a U-bar assembly 300, a distal thigh fixation system 400 (this also operates as a patella fixation system), a shank cradle assembly 500, and heel cradle assembly 600.

Thigh cradle assembly 200 has multiple uses. In at least on embodiment, it elevates, positions and comfortably supports the thigh of the leg to be measured so that the U-bar and shank cradle may be properly interfaced with the leg. In conjunction with the U-bar assembly 300, and the more proximal thigh stabilizing bars, the thigh cradle assembly 200 immobilizes the thigh to prevent movement during laxity testing (manipulation of the tibia relative to the fixed femur). In equipment existing in the market today, the thigh is positioned on a bolster to place the knee at approximately 25 degrees, the bolster typically being a flat piece that does not control in any way for thigh rotation. By contrast, thigh cradle assembly 200 of apparatus 100 includes a shaped thigh cradle 202 and further includes thigh restraint/strapping systems to ensure more consistent positioning of the thigh in the frontal and transverse plane.

Thigh cradle 202 is configured to mirror the natural curvature of the underside of the thigh. In at least one embodiment, thigh cradle 202 is 20.44 cm high and 15.02 cm wide at its distal interfacing edge, while at the proximal edge thigh cradle 202 is approximately 15.13 cm high and 15.5 cm wide. In various embodiments, the width may increase slightly from distal to proximal to accommodate the shape of the thigh. Two sliding clamping arms can be configured to come in from the medial and lateral sides of the more proximal end (closest to the hip) of the thigh cradle to firmly fix the thigh in the cradle and further constrain frontal and transverse plane motion of the femur. Proximal and distal are termed used herein with respect to a patient positioned with a leg extending longitudinally from their body from proximal to distal. Thus, the lower end of the thigh cradle 202 extending toward a patient's torso can be described as proximal, and the higher end extending away from the patient's torso and toward the shank cradle assembly 500 can be described as distal.

In one embodiment, a single thigh strap can be placed at the distal end allowing moderate pressure to be placed on the thigh, thereby compressing it comfortably to help control extraneous thigh movement in the thigh cradle. Along with the shank cradle, it can allow accurate positioning of the knee from 0-30 degrees of flexion. In an alternate embodiment, the single thigh strap is replaced by, or integrated into, a proximal thigh fixation system as described below.

Figure 4:
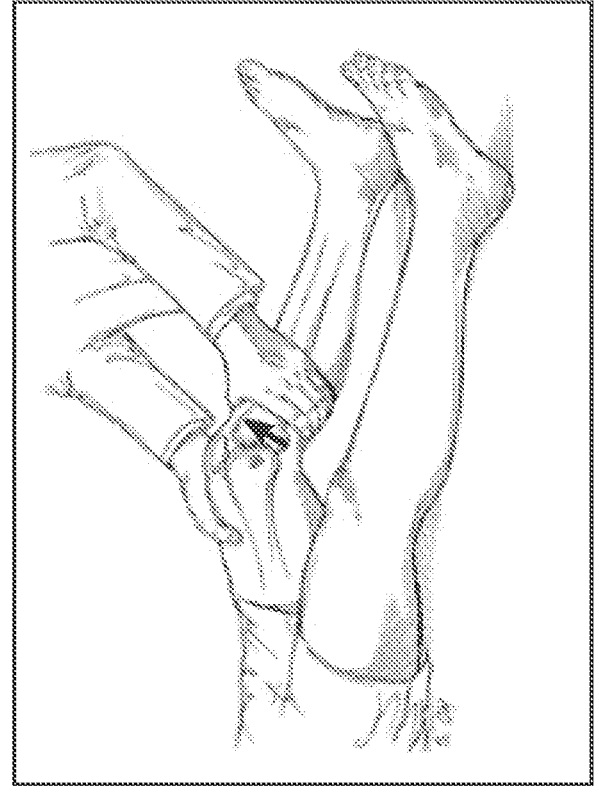
FIG. 4 is a perspective view of the limbs of a patient/subject lying upon a therapy table in a supine position, according to at least one embodiment.

In various embodiments, the thigh cradle is a specific component of the device, the role of the thigh cradle is to reproducibly position and securely hold the patient's thigh during measurement. The thigh cradle is affixed to the device base that will be firmly affixed to a standard treatment table such that it cannot move during measurement or contribute to a patient fall from the therapy table. The patient lies upon the therapy table in the supine position and the patient's leg is placed atop the thigh support of the device. The proximal end of the thigh cradle will be equipped with two posts and a thigh fixation system to stabilize the proximal thigh. The thigh cradle will be high enough off the table to allow for relevant device components to reside underneath it, but not so high that the patient's hips are unseated from the table. The thigh support is also angled in such a way to allow for testing to be completed with a knee angle of approximately 0-30 degrees when measured from full extension (see FIG. 4, for example). The patient's thigh is secured to the thigh cradle in a manner that requires 1 minute or less by the end user.

Figure 2:
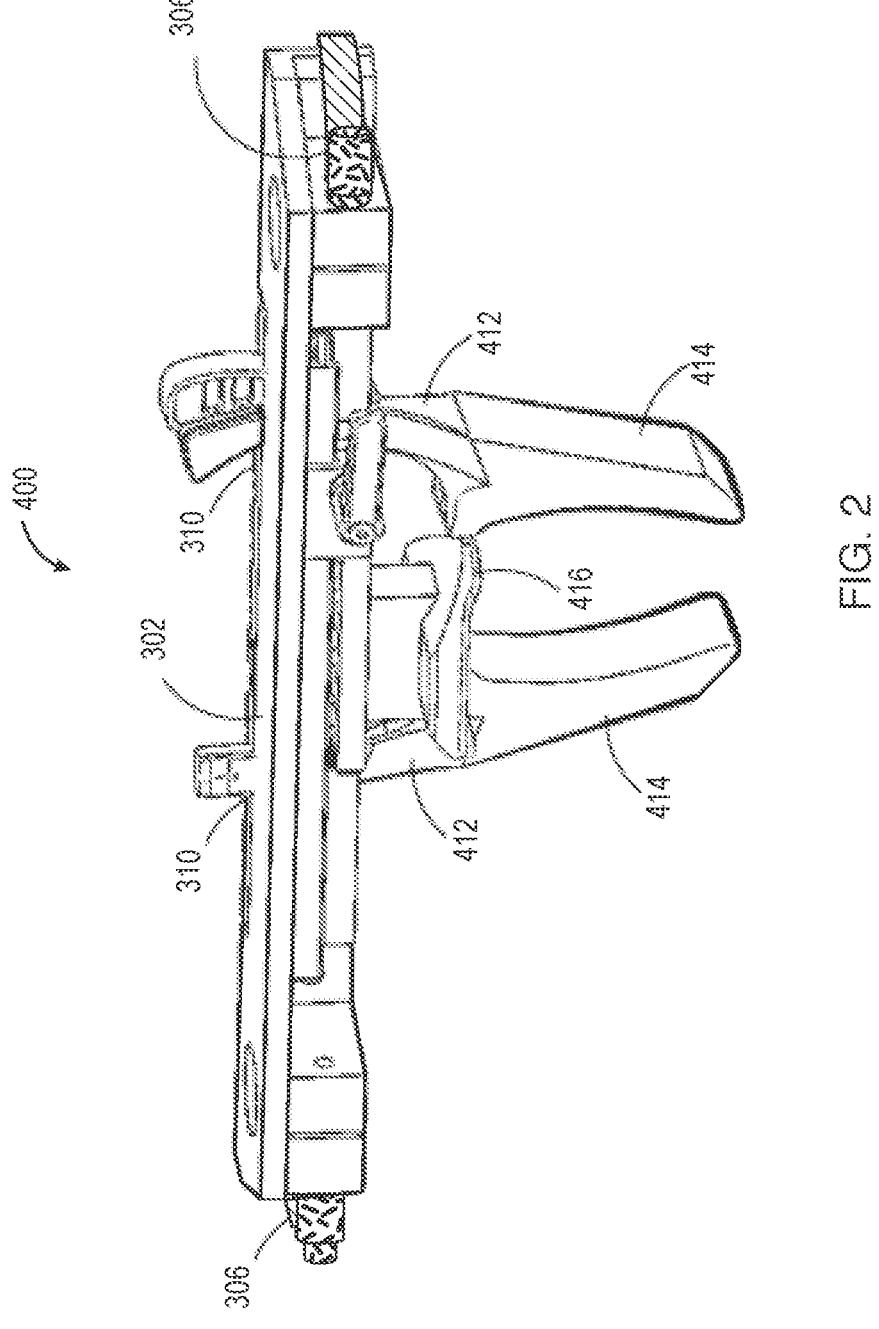
FIG. 2 is a perspective view of the U-bar and thigh fixation components of the testing apparatus of FIG. 1 for illustration purposes, according to at least one embodiment.

U-bar assembly 300 supports the patella pad and distal thigh fixation system 400. Distal thigh fixation system 400 includes two condyle pad adjustment arm 412, each having a downward extending end upon which a respective condyle pad 414 is mounted. The U-bar 302 and thigh fixation system are shown in FIG. 2 removed from other components of the apparatus 100 for illustration purposes. Patella pad 416 is mounted to a linear sliding track that is also mounted to the underside of the U-bar assembly 300. Condyle pad adjustment arm 412 extend from and are adjustable relative to the U-bar assembly 300. Condyle pad adjustment arm 412 each has on its medial face a rubberized condyle pad 414. Each of the two arms/faces are guided by a fully supported linear clamping mechanism which allows for quick-release and fine adjustment by flipping the release valve or squeezing the adjustment trigger, respectively. The adjustment feature allows the condyle pads 414 to be more adjustable to accommodate for a greater amount of condylar widths and heights and configurations. Condyle pads 414 are further configured to be able to adjust up and down for different condylar heights to thereby accommodate different size knees.

U-bar assembly 300 includes a U-bar 302 that is supported by and spans two vertical height adjustment bars 304 (see FIG. 1) approximately between which a patient's knee will be placed in use with the patella pad 416 (se FIG. 2) positioned above the patella of the knee. U-Bar height adjustment clamps 306 are at lateral ends of U-bar 302 to permit vertical movement of the U-bar 302 along the vertical height adjustment bars 304 to a preferred height and then fixation of the U-bar 302 by use of the U-Bar height adjustment clamps 306. Two condyle pad clamps 310 are carried by the U-bar 302. Condyle pad adjustment arms 412 are adjustably connected to the U-bar 302 by way of condyle pad clamps 310. U-bar 302 houses and supports patella pad 416 and condyle clamping system. By interfacing with two vertical height adjustment bars 304 attached to the base 102, the U-bar 302 is able to snug up to the patella and the medial and lateral femoral condyles of the leg being examined and fix itself, compressing and immobilizing the patella in the femoral intercondylar groove and preventing extraneous motion of the femur during testing.

In the illustrated embodiment, U-bar assembly 300 is mounted, by way of vertical height adjustment bars 304, on base 102 independently from thigh cradle assembly 200, which is mounted on base 102 by four riser bars 206 interconnected by a base-end bracket 204. In other embodiments, U-bar assembly 300 and thigh cradle assembly 200 can be mounted together upon the same vertical adjustment or riser bar assembly defining a more consolidated U-bar and thigh cradle assembly.

Together, patella pad 416 (see FIG. 2) and bilateral condyle pads 414 (see FIG. 2) can stabilize the femur in the thigh cradle, preventing movement of the femur during anterior-posterior (AP), varus-valgus (VV) and internal-external rotation (IER) testing. U-bar 302 is designed for superior fixation of the femur. This specific aspect of the apparatus 100 departs from prior devices in multiple ways. Most prior devices are only designed to measure laxity in one plane of motion. To test multiple planes in a single apparatus and patient positioning, stabilization of the thigh is needed such that it remains fixed, whether applying loads in sagittal, frontal or transverse planes. Thus, U-bar 302 can operate to stabilize the contoured patella pad 416 that seats the patella in the femoral groove to thereby stabilize the femur during AP testing. Condyle pads 414 are designed to work together to provide a counterforce against loads in the frontal and transverse plane. Used with patella pad 416 and the thigh cradle assembly, the counterforces created by condyle pads 414 operate to stabilize the thigh during frontal and transverse plane loading of the tibia, which are novel and advantageous to this device.

In at least one embodiment, patella pad 416 has a flat surface that represents a moldable deforming surface that interfaces with the shape of the patella to improve comfort. Accordingly, in one embodiment, the patella pad includes a cushioned, deformable, and/or resilient flat surface which interfaces with the patient's patella to increase comfort and conformity to varying patellar shapes.

In at least one embodiment, U-bar 302 is approximately 36 cm long and 5 cm wide. Two 2.6 cm diameter holes can be provided for interfacing with vertical height adjustment bars 304 at locations that positioned approximately 9" center to center (i.e., approximately 23 cm apart). Two hosting areas for the thigh fixation system lie medial to the holes. Condyle pad adjustment arm 412 are held parallel to the body of the U-bar such that when they are extended the condyle pads 414 will lie approximately 3.8 cm away from the center of the patella pad 416.

In some embodiments, distal thigh fixation system 400 deploys the condyle pads 414, which interface the distal condyles of the femur to the U-bar system. In some alternate embodiments, condyle pads 414 can be tethered to the AP loading mechanism thereby eliminating the need for distal thigh fixation system 400. Distal thigh fixation system 400 is lockable so that the position is maintained during testing. When the clamps are engaged, distal thigh fixation system 400 operates to snug the condyle pads up against the medial and lateral condyles to prevent frontal and transverse plane movement of the proximal thigh during testing. This, together with the proximal clamping arms on the thigh cradle pads, ensures that the femur is firmly fixed for testing.

In various embodiments, condyle pad adjustment arm 412 are linearly extensible shafts that, on their lower ends, interface with condyle pads 414. Each of the two shafts is inserted through a sheath that guides the shaft and allows for angular articulation. Accordingly, condyle pads 414 operate to slide in to accommodate different widths, and slide up and down to accommodate different heights. In other words, condyle pads 414 will slide in to accommodate different widths, and slide up and down to accommodate different heights. Furthermore, each clamp may be fixated/locked so that the positioning of the clamping system is stable throughout the duration of testing.

The condyle pads 414 provide a comfortable, yet rigid interface between the thigh fixation system and the patient's medial and lateral distal femoral condyles to prevent femoral movement during VV and IER testing. The condyle pads 414 are a contoured such that they interface with the rounded condyles of the distal femur. The surface of the contoured pad is coated with a substance that is firm, pliable and tacky (e.g., silicone rubber) so as to promote a secure interface between the rigid body of the pad and the condyles.

According to various embodiments, patella pad 416 seats the patella within the femoral intercondylar groove by applying compression to the patellar bone when the leg is in approximately 20-30 degrees of flexion. According to some embodiment, patella pad 416 may not be contoured and instead be in the form of a flat pate so that it can accommodate all the different size patellas. In other words, patella pad 416 may be contoured in some embodiments and may not be contoured in other embodiments.

Accordingly, in at least one embodiment, patella pad 416 can be flat on its interfacing edge. This design was chosen to best compress the patella and allow maximal flexibility in a range of patient shapes/sizes. In at least one embodiment, patella pad 416 can include a rubberized surface that interfaces with a patient's patella to increase comfort and conformity to varying patellar shapes. Furthermore, patella pad 416 is connected to U-bar 302 at an adjustable distance to create a rigid point of contact through which compression may be applied by adjusting the position of U-bar 302 along vertical height adjustment bars 304. Patella pad 416 is also configured to be adjustable in the medial and lateral direction to ensure proper alignment and compression of the patient's patella once properly positioned in thigh cradle 202.

Heel cradle assembly 600 (see FIG. 1) operates to secure the lower limb so that force application from the heel cradle 602 can be effectively transferred into the lower limb. According to some embodiments, both Internal-External rotation and varus-valgus rotation laxity tests can have their load application through the heel cradle 602, so it must have a snug interface with the patient's ankle and foot. In some alternate embodiments, the load application can occur from the proximal region.

Accordingly, in various embodiments, heel cradle assembly represents the tibia, ankle and foot fixture. The heel cradle acts as a virtual extension of the patient's leg, maximizing force transfer to the patient's lower leg, ensuring accurate and reliable force transfer ultimately minimizing measurement error. In one embodiment, heel cradle assembly 600 comprises an actuated track upon which a carriage is mounted. However, this feature is optional in that in some embodiment heel cradle assembly does not include an actuated track.

The system operates to secure the foot, ankle and lower leg such that it moves as one unit to reduce movement artifact. Moreover, heel cradle 602, much like thigh cradle 202, is designed to control and standardize the amount of tibial rotation, which can have a significant impact on laxity measurements. It is to be noted that tibial rotation has not been controlled for in prior devices designed for AP or VV laxity testing. Heel cradle 602 is configured to be adjustable in the transverse plane so that the tibia can be positioned such that the tibiofemoral joint is in neutral rotation, and then locked in this neutral orientation during AP and VV testing for accurate and repeatable results.

Heel cradle 602 may at least partially resemble an orthopedic walking boot in some embodiments. To accommodate various shank (tibia) lengths, the distal attachment of the footplate can be extendable. To this end, heel cradle 602 can be extended to the correct length, then locked in place so that it remains rigid during testing. This component itself can also be rigid to avoid bending during V/V and I/E testing.

The shank cradle assembly 500 for AP testing includes shank cradle 502 and A/P actuator apparatus 504. In some embodiments, shank cradle 502 (proximal to the heel cradle) interfaces with the proximal lower leg, just below the joint line, so that anterior/posterior translational laxity tests may be performed. By using the force actuator(s), the weight of the limb can be determined prior to testing so that load can be offset that load to achieve a neutral, zero-shear load starting position from which to determine anterior displacement and posterior displacement from this zero-reference position. The Interface between the A/P actuator apparatus 504 and the leg is the contoured shank cradle, which may be padded, and in at least one embodiment is approximately 50 mm long with an approximately 67.5 mm radius of curvature. To perform posterior testing a strap can provide compression over the top of the shank. The strap can connect on opposite sides of the cradle and may be non-elastic.

A/P actuator apparatus 504 can apply anterior-to-posterior and posterior-to-anterior directed load to the proximal shank (with the thigh stabilized) in a manner similar to a manual Lachman's test. A/P actuator apparatus has, in at least one embodiment, at least 2 cm of action (see data provided in Table 1 further below in this document). A/P actuator apparatus 504 that can be linear will apply anterior directed load to the proximal shank through the calf cradle that interfaces with the gastrocnemius. Posterior loading (pulling) of the limb can be aided by the strap which fastens over top of the shank to enable the shank to be manipulated both anteriorly and posteriorly. In at least one embodiment, the goal is to apply up to 150 N anterior directed loads and 100 N posterior directed loads. A potentiometer or similar measurement device affixed at the tibial tuberosity can operate to measure relative displacement of tibial relative to the patella (femur). In the same embodiment or in a different embodiment, the goal may further comprise applying a fixed load and measuring the displacement at that load. The measured displacement is analogous to what is written for VV and IER below.

Heel cradle apparatus 600 serves as an interface for varus-valgus (VV) rotation actuation. An actuated VV track 604 lies perpendicular to the long edge of the base 102. VV track 604 represents a horizontal track that allows the shank to move in varus-valgus directions. The track 604 is actuated, for example by an integrated stepper motor, which allows for precise movement control. The track controls a carriage 606, which represents a platform that allows for heel cradle 602 and other components to be fastened to it. It should be noted that varus-valgus loads could also be applied manually along the track.

The VV interface can actuate the lower leg shank from its distal end (via the heel cradle) in a curvilinear motion whose radius corresponds to that of the leg being measured. This will allow the lower limb to move in a natural arc as the tibia is rotated relative to the femur in the frontal plane. The novel design allows this arc to be adjusted to each individual's leg length so that there is no binding or compression at the tibiofemoral joint that would impede laxity testing. This provides greater comfort and relaxation for the patient, and thus a more accurate and repeatable measurement of laxity.

Linear track 610 is directly attached perpendicularly to the carriage 606 of the VV track 604. Heel cradle 602 attaches directly to an internal-external or IE rotational fixture 612. IE rotational fixture 612 is attached directly to the VV carriage 606 and separately to the linear track 610. In at least one embodiment, IE rotational fixture 612 mounted on the carriage via a linear track facilitates varus-vargus laxity testing. The linear track allows the heel cradle to move in varus-valgus direction.

Actuated VV track 604 is used to deflect the knee approximately 30 degrees, 15 degrees to each side (see data in Table 1). This will be different for each person and it represents the maximum displacement expected—the goal is to apply a 0-10 Nm torque and measure the amount of displacement, rather than move to a specific displacement. The VV track 604 is a linear track with driver. Perpendicular to this track, attached to the carriage 606 is the smaller linear track 610 that is unactuated, low friction, and lockable. This piece is to be used to adjust the VV actuator for varying leg size. To create an arc from this linear motion an additional low friction track may be used in parallel to the aforementioned one to allow for natural movement of the limb along its arc radius. The linear track 610 permits length adjustment, and the carriage 606 is laterally movable along VV track 604 by the VV track actuator (i.e., the aforementioned stepping motor in at least one embodiment). In some alternate embodiments, the carriage 606 is laterally movable along VV track 604 manually by the clinician, for example.

IE rotational fixture 612 serves as mount and rotational system which holds heel cradle 602 in place and allows for rotational tests to be conducted via a lockable/unlockable pin (so that it can be locked during VV and AP Loading and unlocked during IE loading). One of the greatest challenges with IE Laxity is fixation of the femur during testing, which is addressed with the U-bar thigh stabilization system.

Accordingly, in various embodiments, thigh stabilization is accomplished by a patella/condyle fixture. The patella/condyle fixture works in conjunction with the thigh cradle to ensure that the patient's distal thigh does not shift during the measurement operation of the product. This is advantageous, as system 700 and/or apparatus 100 will measure displacement of the lower leg relative to the affixed thigh. The fixture is properly positioned by the end user on three anatomical points of the patient's distal femur: the patella, lateral epicondyle and medial epicondyle. Properly positioned, the fixture is then adjusted to the patient such that sufficient force is applied to the patella and epicondyles to stabilize the thigh without causing pain or injury to the patient.

IE rotational fixture 612 includes a body 614, a rotary shaft 616, and a footplate connector 620. Body 614 connects to linear track 610 below such that it can be adjusted to different leg lengths. A hole fitted for a bearing allows the rotary shaft of an IE actuator 622 to pass through it. IE actuator 622 is attached to the body to allow rotation of the shaft. The footplate connector is then fastened to the end of the rotary shaft such that the shaft (axis of rotation) is collinear to the tibia of the measured leg, when positioned correctly.

IE actuator 622 can rotate through the long axis of the heel cradle assembly 600—available range can be at least 50 degrees and may be 60 degrees (see data in Table 1). In at least one example, IE actuator 622 can be a stepper motor able to create at least 0-5 Nm of torque about its axis of rotation, and may have at least a plurality of steps.

Devices and methods of use thereof as described and enabled herein can be used by physicians (family practice, orthopedic), physician assistants, athletic trainers, physical therapists and other allied health professionals to examine joint integrity to assess injury risk (pre-injury screening), following injury (acute and chronic disease progression), therapeutic results during post-surgical recovery, and rehabilitation. Non-limiting specific applications include:

Characterization of laxity profiles in healthy and diseased knees;

Monitoring changes in knee laxity with maturation;

Screening to identify excessive knee joint laxity in the physically active to identify those at risk for ACL injury;

Monitoring disease progression in those with osteoarthritis and other relevant joint diseases;

Providing normative data across age (child to older adult) and sex for injury risk screening and satisfactory restoration of function post injury and surgery;

Injury Diagnosis;

Positioning of joint for radiological examination for stress testing;

Objective assessment of injured and un-injured knees to assess ligament integrity (cruciate ligaments and collateral ligaments) and confirm extent of joint instability or "play" following injury without the need for X-ray;

Post Surgical Repair;

Confirmation of proper ligament tensioning during surgical reconstruction

Monitoring ligament healing post ligament repair or reconstruction;

Training and rehabilitation interventions;

Monitoring improvements in joint laxity with therapeutic interventions (e.g. strength training, positive ligament loading);

Training tool to induce positive ligament adaptations from applied loads;

Monitor ligament healing (primary healing and during rehabilitative process);

Custom fitting of knee braces and other knee orthoses designed to protect ligaments and limit knee motion;

Excellent tool for research laboratories interested in quantifying the laxity and stiffness profiles of the knee to advance knowledge in all areas noted above;

Deploying in the field (e.g. military theatre) to diagnose ligament injury when sophisticated imaging devices are inaccessible;

Providing the most comprehensive assessment of joint laxity available on the market (current clinical devices are limited to anterior posterior assessment of joint laxity or rotational laxity).

Table 1 below provides the mean, standard deviation, and range values for clinical measurement of AP, VV and IER Laxity. Descriptive statistics provided in Table 1 include: AKL=anterior knee laxity; PKL=posterior knee laxity; VAR=varus rotational knee laxity; VAL=valgus rotational knee laxity; ER=external rotational knee laxity; IR=internal rotational knee laxity; VARVAL=total varus-valgus rotational knee laxity; and, IER=total internal-external rotational knee laxity.

TABLE 1

| | N | Minimum | Maximum | Mean | Std. Deviation |
|---|---|---|---|---|---|
| AKL_M | 141 | 3.0 | 13.0 | 6.734 | 1.9300 |
| AKL_L | 122 | 3.0 | 13.8 | 7.137 | 2.0072 |
| CAKL_M | 141 | 3.00 | 12.66 | 6.7378 | 1.90621 |
| CAKL_L | 122 | 3.00 | 13.73 | 7.0645 | 2.01787 |
| CPKL_M | 119 | −2.96 | −.88 | −1.7410 | .42378 |
| CPKL_L | 102 | −3.12 | −.84 | −1.7231 | .40086 |
| VAR_M | 141 | −11.8 | −2.1 | −5.337 | 1.6669 |
| VAR_L | 121 | −9.4 | −1.6 | −5.262 | 1.6929 |
| VAL_M | 141 | 2.0 | 13.3 | 6.361 | 1.9948 |
| VAL_L | 121 | 1.9 | 12.5 | 6.101 | 2.2023 |
| ER_M | 141 | 5.8 | 33.0 | 14.729 | 4.9005 |
| ER_L | 121 | 5.0 | 29.9 | 14.543 | 4.9120 |
| IR_M | 141 | −27.9 | 1.1 | −10.162 | 4.8302 |
| IR_L | 121 | −29.8 | 1.4 | −9.676 | 5.4394 |
| VARVAL_M | 141 | 5.4 | 24.3 | 11.698 | 3.2639 |
| IER_M | 141 | 7.4 | 53.0 | 24.890 | 8.1057 |
| VARVAL_L | 121 | 3.6 | 21.5 | 11.363 | 3.5061 |
| IER_L | 121 | 7.4 | 48.8 | 24.220 | 8.2560 |
| Valid N (listwise) | 98 | | | | |

Figure 3:
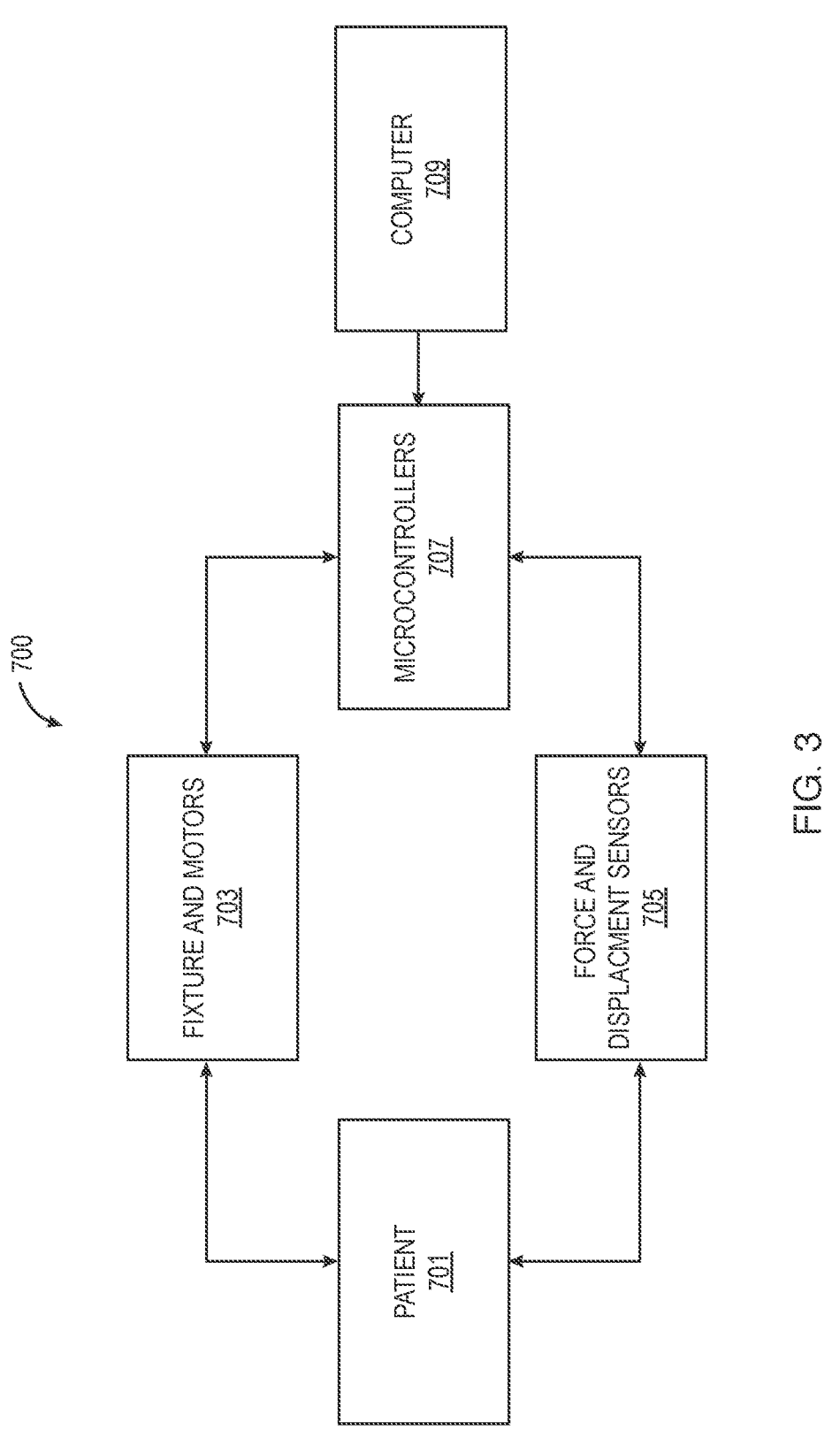
FIG. 3 is a schematic representation of a system for carrying out a multi-axial joint laxity testing using a multi-axial joint laxity testing apparatus, according to at least one embodiment.

In various embodiments, the system including multi-axial joint laxity testing apparatus 100 as disclosed herein can further comprise various components including a patient interface, hardware and software components. Accordingly, in various embodiments, the system such as system 700 as illustrated in FIG. 3 can provide for an ergonomic interface between the knee of a patient 701 and the components of apparatus 100 and/or of system 700 such as fixture and motors 703 that apply force to the patient's knee as well as force and displacement sensors 705. Apparatus 100 itself (or the system that includes a device such as apparatus 100) records and analyzes the resulting displacement with one or more microcontrollers 707 in communication with, or forming part of, a computer 709. Computer 709 continuously monitors force and displacement via force and displacement sensors 705 during the test period while controlling the fixture and motors 703 that apply the force required to create displacement. The patient 701 is made to be fully relaxed during the test such that the patient 701 makes no effort to resist the applied force. The product fixture and motors 703 may be directly controlled by the force and displacement sensors 705 as a "fail-safe" in the event of failure of computer 709 that could create harm to patient 701. The apparatus and the system can also be manually driven using the force sensor readouts.

With regard to feedback display, during measurements of laxity, the relationship of mechanical displacement to force applied is determined and displayed on a visual display device coupled to the system or to apparatus 100. Subjectively, this relationship may otherwise be assessed visually and by "feel" that the end user subjectively experiences. The objective measurement made by the system and device as disclosed herein is achieved by essentially curve-fitting discrete recording of force as the actuators displace the patient's knee during the test period. These measurements are typically displayed in a simple graph as a hysteretic path as shown, for example, in FIG. 5.

With regard to interface options, the end users that use the system/device is expected to include both technical and non-technical end users. Whereas technical end users may welcome the kind of data presented above, the non-technical user too may appreciate simpler interface such as key numeric test results with the "normal" range of the test. Automatic notices of possible test errors will further ensure high quality results. To appeal to both types of end users, in at least one embodiment, the display will include a "standard" and "advanced" display option that is selectable by the end user.

The tables below describe and define the general requirements of the system/device and are intended to capture end user needs and to guide engineers in the development of technical solutions according to at least one embodiment of the presently disclosed subject matter. The mechanical aspects of the system and device as described herein according to at least one embodiment are provided in Table 2 below.

TABLE 2

| Item | Value | Notes |
|---|---|---|
| Size | 18 in wide × 48 in long × 24 in high | As small a footprint as is possible, e.g., within 28 inches by 72 inches-the dimensions of a typical therapy table. The device may be in daily use and so would not require regular break-down and storage, however, space is typically at a premium in institutions and so smaller is better. The device/system will be reasonably light and portable and can be placed (and removed from a treatment table as needed) and which could also be used in the field. |
| Weight | 25 lbs. or less | The maximum allowable weight for a checked domestic economy bag is typically 50 pounds. While this weight may establish the maximum device weight, a lower weight is desired because the device may likely be moved regularly by the end user or her staff (e.g. on and off an available examination table or to and from storage). |
| Materials | | The non-consumable device components can be chosen to hold up under daily use for a period of at least 5 years' time. Such components include the base, thigh support, knee stabilization parts, sensors and motors. Materials shall be non-toxic and resistant to degradation from common cleaning agents such as bleach, proprietary disinfectants and ultraviolet lamps. |

TABLE 2-continued

| Item | Value | Notes |
|---|---|---|
| | | Certain mechanical components of the system/device such as, for example, straps and pads may be single use or "consumable". Although the device is not being designed to work within an MRI environment, efforts to avoid or minimize the use of metal is preferred in part for MRI interests but also weight reduction. |

The electrical aspects of the system and device as described herein according to at least one embodiment are provided in Table 3 below.

TABLE 3

| Item | Value | Notes |
|---|---|---|
| Voltage | 120 VAC and 220 VAC | The ability to use 120 VAC and 220 VAC power sources is proposed to help address a wider market (e.g. hospitals, clinics, private practice) |
| Current | Amps | Electrical current will depend upon the specific electromechanical and computer components required to achieve end user needs. |
| Power | Watts | Power will depend upon the voltage and current specifications of the specific electromechanical and computer components, however, sufficient power for startup and "peaks" encountered during use of the product shall be ensured. |

The safety aspects of the system and device as described herein according to at least one embodiment are provided in Table 4 below.

TABLE 4

| Item | Value | Notes |
|---|---|---|
| Electrical Isolation | | The system/device design shall ensure that it does not present an electrical safety issue to the end user, patient or any party that may come into contact with the device (e.g. administrative staff, facilities maintenance personnel). The system/device shall comply with all existing safety standards for medical devices. |
| Force Limitation | ±150 N AP force | The system/device is configured to be able to generate sufficient force on the patient knee joint to displace the joint for clinical evaluation. Such force, however, needs to be constrained such that no injury is made to the patient's knee by the device. |
| | ±5 N · m IE torque | Safety of patients' joint shall be ensured by redundant failure protection such as in the software, at the motor interface and other methods that ensure a tendency for the device to safely "stall" its movement rather than to exceed safe forces and joint displacement. |
| | ±10 N · m VV moment | The proposed forces are placeholders only and are based on the values provided in the publication Male-Female Differences in Knee Laxity and Stiffness: A Cadaveric Study, Am J Sports Med. 2015 December; 43(12): 2982-7. [online as of 18 Jul. 2018; https://www.ncbi.nlm.nih.gov/pubmed/26464493]. The proposed forces represent the clinical force limits used for testing, thus actual force limits of the device will be slightly beyond these. |
| General | | General safety design shall be configured to address basic, "common sense" elements, including but not limited to elimination pinch points, sharp edges, abrasive surfaces, and excessive fixture force (i.e., ability to make a mechanical adjustment that could cause injury to the knee joint or cause a measurement error). Attention shall be given to how the system/device is affixed to a treatment table such that it cannot shift during use or lead to a patient fall from the therapy table. |

The user interface of the system and device as described herein according to at least one embodiment are provided in Table 5 below.

TABLE 5

| Item | Value | Notes |
| --- | --- | --- |
| Mechanical fixtures and adjustments | | Includes all those mechanical components required to align and secure the patient's leg and knee during laxity measurement by the product. |
| Thigh fixture Patellar fixture Condyle fixtures | Setup in 3 minutes or less N maximum force | Manual adjustments can be reliably made in a quick and effortless fashion, so the end user can focus on the patient and operation of the computer for test. Adjustments shall maintain fixture during the entire duration of the measurement but without cause undue discomfort to the patient or create any injury to the patient. |
| Electromechanical activators | | Includes all those components that are controlled by the computer software during measurement, those sensors that provide feedback to the computer during operation, and those devices that enable the computer control of electromechanical components. |
| Stepper motors Displacement sensors Force sensors | 3 cm maximum linear displacement (A/P) 30-degree maximum (V-V) rotational (along an arc that is approximately equal to the average male) displacement and 15 degree maximum (I/E) rotational displacement N maximum force Linear displacement rate Rotational displacement rate | Needs three separate motors, one for each testing motion. At least three load sensors and at least two displacement sensors may be provided in one embodiment. Rate of displacement shall occur within a range that both meets the goals of patient safety and of short test times. |
| Controls | | Controls include all those components required to initiate operation and control the product during measurement, specifically a computer keyboard, mouse, touch-screen and optional remote event marker |
| Computer keyboard, mouse and touch screen Mains power switch Event/remote switch | | Configure to run Windows 10 or higher operating system. Integrated keyboard and mouse, or wireless keyboard and mouse to eliminate wires. One central main power switch is provided that disables all power to the non-computer electrical components (e.g. motors, sensors) Remote key (optional) that annotates an event marker in the data set being collected during test |
| Feedback | | Feedback includes all those components required to provide the end user with guidance on and confirmation of proper product performance |
| Computer display Audio/visual alerts Printed reports | | |

The data analysis, storage, and transmission aspects of the system and device as described herein according to at least one embodiment are provided in Table 6 below.

TABLE 6

| Item | Value | Notes |
| --- | --- | --- |
| System calibration | | Some form of simple two-point calibration to ensure that the force and displacement sensors used for the measurement are working properly and with design tolerances. |
| Sampling rate | | Sample rate that provides sufficient resolution for accurate analysis as provided, for example, in http://mathworld.wolfram.com/NyquistFrequency.html |
| Sensor resolution | | The analog and digital resolution of sensors need to be adequate to ensure accurate analysis. The sensors may have a resolution as indicated in http://www.lionprecision.com/tech-library/technotes/article-0010-sensor-resolution.html |

TABLE 6-continued

| Item | Value | Notes |
|---|---|---|
| Computer hardware and operating system | Intel i5 processor or higher, or other Windows compatible processor (e.g. AMD) | Intel-based with touchscreen and Windows 10. Configuration is intended to help ensure that many off-the-shelf computers may be incorporated into the product solution rather than to require a proprietary computer platform |
| Local storage | 16 Mb RAM 500 Gb HDD or SSD | RAM storage installed in the computer to run software and hold data being collected and analyzed (default is 16 Mb) Hard drive or other storage on the computer that maintains patient data (default is 500 Gb) |

As disclosed herein, a system for knee joint laxity testing comprises: a knee joint laxity testing apparatus engageable with a person's knee, the knee joint laxity testing apparatus comprising a thigh cradle assembly, a shank cradle assembly, and a heel cradle assembly, the knee joint laxity testing apparatus configured to measure knee laxity values in three planes of motion. A controller is coupled to the knee joint laxity testing apparatus, the controller configured to receive the measured knee laxity values in three planes of motion. An application is configured to display, on a user interface of a computing device such as computer 709, the measured knee laxity values in three planes of motion.

According to at least one embodiment, the computer 709 (i.e., the computing device) comprises a processor communicably coupled to at least one memory; and program instructions which when executed by the processor cause the processor to: receive, from the controller, the measured knee laxity values in three planes of motion; and, display, on the user interface of the computing device, a level of deviation of a measured knee laxity value from a predetermined value. The controller such as microcontroller 707 is in communication with at least one motor configured to perform one of: the anterior-posterior translations; the varus-valgus rotations; and the internal-external rotations.

According to one or more embodiments, microcontroller 707 is in communication with at least one sensor such as force and displacement sensor 705 configured to sense one or more of a force and a displacement resulting from one of: the anterior-posterior translations; the varus-valgus rotations; and the internal-external rotations.

According to one or more embodiments, the system further comprises a patella, a thigh fixation system positioned between the thigh cradle assembly and shank cradle assembly, and at least two clamping arms coupled to thigh cradle assembly for securing a thigh positioned on the thigh cradle assembly.

According to one or more embodiments, the system further comprises receiving, from the controller, the measured knee laxity values in three planes of motion; and, displaying, on the user interface of a computing device, a level of deviation of a measured knee laxity value from a predetermined value.

According to one or more embodiments, the controller such as microcontroller 707 communicates with at least one motor performing one of: the anterior-posterior translations; the varus-valgus rotations; and the internal-external rotations. According to one or more embodiments, microcontroller 707 communicates with at least one sensor configured to sense one or more of a force and a displacement resulting one of: the anterior-posterior translations; the varus-valgus rotations; and the internal-external rotations.

As disclosed herein, a method for measuring knee laxity with a knee joint laxity testing apparatus comprises: measuring knee laxity values in three planes of motion with a knee joint laxity testing apparatus engageable with a person's knee, wherein the knee joint laxity testing apparatus comprises a thigh cradle assembly, a shank cradle assembly, and a heel cradle assembly, receiving at a controller coupled to the knee joint laxity testing apparatus the measured knee laxity values; and, displaying, on a user interface of a computing device, the measured knee laxity values.

Various components of a system according to the exemplary embodiments such as system 700 may be embodied in a program command form which may be executed through various computer units and recorded in computer-readable media. The computer-readable media may contain program commands, data files, data structures, and combinations thereof. The program commands recorded in the medium may be specially designed for the exemplary embodiments. Alternatively, the program commands may be well-known by those skilled in computer software. The computer-readable media may include hardware devices specially configured to store and execute program commands. For example, magnetic media, such as a hard disk, a floppy disk and a magnetic tape, optical media, such as a CD-ROM and a DVD, a magneto-optical media, such as a floptical disk, a ROM, a RAM and a flash memory may be used as the computer-readable media. The program commands may include a machine language prepared by a compiler and a high-level language code prepared by an interpreter so as to be executed by a computer. The above-mentioned hardware devices may be configured to operate as one or more software modules to operate the exemplary embodiments and vice versa. As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium (including, but not limited to, non-transitory computer readable storage media). A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter situation scenario, the remote computer may be connected to the user's computer through any type of network, including a local area network (LAN) or a wide area network (WAN), or the connection may be made to an external computer (for example, through the Internet using an Internet Service Provider). These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Any dimensions expressed or implied in the drawings and these descriptions are provided for exemplary purposes. Thus, not all embodiments within the scope of the drawings and these descriptions are made according to such exemplary dimensions. The drawings are not made necessarily to scale. Thus, not all embodiments within the scope of the drawings and these descriptions are made according to the apparent scale of the drawings with regard to relative dimensions in the drawings. However, for each drawing, at least one embodiment is made according to the apparent relative scale of the drawing.

Particular embodiments and features have been described with reference to the drawings. It is to be understood that these descriptions are not limited to any single embodiment or any particular set of features, and that similar embodiments and features may arise or modifications and additions may be made without departing from the scope of these descriptions and the spirit of the appended claims.

As to the above, they are merely specific embodiments of the present invention; however, the scope of protection of the present invention is not limited thereto, and within the disclosed technical scope of the present invention, any modifications or substitutions that a person skilled in the art could readily conceive of should fall within the scope of protection of the present invention. Thus, the scope of protection of the present invention shall be determined by the scope of protection of the appended claims.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

These and other changes can be made to the disclosure in light of the Detailed Description. While the above description describes certain embodiments of the disclosure, and may describe the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features, or aspects of the disclosure with which that terminology is associated. In general, the terms used in the following claims should not be construed to limit the disclosure to the specific embodiments disclosed in the specification, unless the above Detailed Description section explicitly defines such terms. Accordingly, the actual scope of the disclosure encompasses not only the disclosed embodiments, but also all equivalent ways of practicing or implementing the disclosure under the claims.

What is claimed is:

1. A knee joint laxity testing apparatus comprising:
    a base comprising a proximal end and a distal end opposed to the proximal end;
    a thigh cradle assembly mounted to the base adjacent the proximal end;
    a U-bar assembly mounted to the base distally to the thigh cradle assembly,
        wherein the U-bar assembly comprises two vertical bars each having a first end affixed to the base in a stationary position and a second end extending away from the base, a base member configured to span the two vertical bars, and two height adjustment clamps, wherein each of the two height adjustment clamps are disposed adjacent one of opposed lateral ends of the base member and configured to slidably engage one of the two vertical bars such that the base member can slidably move relative to and along a length of the two vertical bars between the first end and second end thereof;
    a shank cradle assembly disposed distally to the U-bar assembly along the base,
        wherein the shank cradle assembly comprises a contoured shank cradle having a concave top surface configured to contact a calf of a leg, and an opposed bottom surface, and wherein the shank cradle assembly further comprises a linear actuator having a selectively movable action end attached to the bottom surface of the shank cradle and a bottom end, opposite to the action end, affixed to the base such that the linear actuator is vertically aligned between a portion of the base and a portion of the shank cradle and a line perpendicular to the base extends through the concave top surface and bottom surface of the shank cradle and selectively movable action end of the linear actuator; and
    a heel cradle assembly mounted to the base distally to and separately from the shank cradle assembly,
        wherein the apparatus is configured to measure knee laxity in three planes of motion.

2. The apparatus of claim 1, wherein the three planes of motion comprise anterior-posterior translations; varus-valgus rotations; and internal-external rotations.

3. The apparatus of claim 1, wherein the thigh cradle assembly further comprises a thigh cradle having a concave shaped curvature and at least two clamping arms coupled to the thigh cradle on a proximal end thereof opposite a distal end thereof, which is closest to the U-bar assembly, and wherein the clamping arms are configured for securing a thigh positioned against the concave shaped curvature of the thigh cradle.

4. The apparatus of claim 3, further comprising a patella pad mounted along and extending away from a bottom surface of the base member of the U-bar assembly and a distal thigh fixation system mounted to the base member and having at least a portion extending away from the bottom surface thereof, wherein the bottom surface of the base member is disposed closest to the base of the apparatus.

5. The apparatus of claim 4, wherein the distal thigh fixation system comprises two condyle pads, wherein each of the two condyle pads is attached to and guided by a respective condyle pad adjustment arm, wherein the respective condyle pad adjustment arm is disposed through the base member and a respective condyle pad is affixed to a downward extending end of the respective condyle pad adjustment arm, wherein the downward extending end is disposed furthest away from the bottom surface of the base member relative to other portions of the respective condyle pad adjustment arm.

6. The apparatus of claim 5, wherein the two condyle pads are configured to be adjustable along a first line perpendicular to the bottom surface the base member and along a second line parallel to the bottom surface of the base member.

7. The apparatus of claim 5, wherein the U-bar assembly further comprises a linear track disposed adjacent to and along the bottom surface, extending between the lateral ends, wherein the patella pad is slidably affixed to the linear track and wherein the linear track is configured to allow the patella pad to move between the lateral ends.

8. The apparatus of claim 4, wherein the patella pad has a contact surface configured to be moved along a line perpendicular to the bottom surface of the base member and selectively locked at various points along the line at various distances away from the bottom surface.

9. The apparatus of claim 3, wherein a diameter of the concave shaped curvature of the thigh cradle narrows diametrically from the proximal end thereof to the distal end thereof.

10. The apparatus of claim 8, wherein the contact surface of the patella pad is at least one of cushioned, deformable, and resilient.

11. The apparatus of claim 1, wherein the linear actuator is affixed to the base between the U-bar assembly and a heel cradle of the heel cradle assembly.

12. The apparatus of claim 1, wherein the heel cradle assembly further comprises an internal-external (IE) rotational fixture mounted on a carriage, and a heel cradle mounted on the IE rotational fixture.

13. The apparatus of claim 12, wherein the carriage has a bottom surface mounted to a first linear track extending in a direction perpendicular to a line extending through the proximal end and distal end of the base to facilitate varus-valgus laxity testing.

14. The apparatus of claim 13, wherein the heel cradle is mounted on the IE rotational fixture via a rotary shaft and further comprising a second linear track affixed to a top surface of the carriage, wherein the top surface of the carriage is opposite the bottom surface and the second linear track is shorter in length than the first linear track and extends in a direction perpendicular to the first linear track and parallel to the line extending through the proximal end and distal end of the base.

15. A system for knee joint laxity testing, the system comprising:

a knee joint laxity testing apparatus engageable with a person's knee, the knee joint laxity testing apparatus comprising a base comprising a proximal end and a distal end opposed to the proximal end, a thigh cradle assembly mounted to the base adjacent the proximal end, a U-bar assembly mounted to the base distally to the thigh cradle assembly, wherein the U-bar assembly comprises two vertical bars each having a first end affixed to the base in a stationary position and a second end extending away from the base, a base member configured to span the two vertical bars, and two height adjustment clamps, wherein each of the two height adjustment clamps are disposed adjacent one of opposed lateral ends of the base member and configured to slidably engage one of the two vertical bars such that the base member can slidably move relative to and along a length of the two vertical bars between the first end and second end thereof, a shank cradle assembly disposed distally to the U-bar assembly along the base, wherein the shank cradle assembly comprises a contoured shank cradle having a concave top surface configured to contact a calf of a leg, and an opposed bottom surface, and wherein the shank cradle assembly further comprises a linear actuator having a selectively movable action end attached to the bottom surface of the shank cradle and a bottom end, opposite to the action end, affixed to the base such that the linear actuator is vertically aligned between a portion of the base and a portion of the shank cradle and a line perpendicular to the base extends through the concave top surface and bottom surface of the shank cradle and selectively movable action end of the linear actuator, and a heel cradle assembly mounted to the base distally to and separately from the shank cradle assembly, wherein the knee joint laxity testing apparatus is configured to measure knee laxity values in three planes of motion;

a controller coupled to the knee joint laxity testing apparatus, the controller configured to receive the measured knee laxity values in three planes of motion; and the controller further configured to display, on a user interface of a computing device, the measured knee laxity values in three planes of motion.

16. The system of claim 15, wherein the computing device comprises a processor communicably coupled to at least one memory; and program instructions which when executed by the processor cause the processor to:

receive, from the controller, the measured knee laxity values in three planes of motion; and display, on the user interface of the computing device, a level of deviation of a measured knee laxity value from a predetermined value.

17. The system of claim 15, wherein the three planes of motion comprise anterior-posterior translations; varus-valgus rotations; and internal-external rotations.

18. The system of claim 17, wherein the controller is in communication with at least one motor configured to perform one of: the anterior-posterior translations; the varus-valgus rotations; and the internal-external rotations.

19. The system of claim 18, wherein the controller is in communication with at least one sensor configured to sense one or more of a force and a displacement resulting from one of: the anterior-posterior translations; the varus-valgus rotations; and the internal-external rotations.

20. The system of claim 15, wherein the thigh cradle assembly further comprises a thigh cradle having a concave shaped curvature and at least two clamping arms coupled to thigh cradle on a proximal end thereof opposite a distal end thereof, which is closest to the U-bar assembly, and wherein the clamping arms are configured for securing a thigh positioned against the concave shaped curvature of the thigh cradle.

21. The system of claim 20, further comprising a patella pad mounted along and extending away from a bottom surface of the base member of the U-bar assembly and a distal thigh fixation system mounted to the base member and having at least a portion extending away from the bottom surface thereof, wherein the bottom surface of the base member is disposed closest to the base of the apparatus.

22. The system of claim 21, wherein the distal thigh fixation system comprises two condyle pads, wherein each of the two condyle pads is attached to and guided by a respective condyle pad adjustment arm, wherein the respective condyle pad adjustment arm is disposed through the base member and a respective condyle pad is affixed to a downward extending end of the respective condyle pad adjustment arm, wherein the downward extending end is disposed furthest away from the bottom surface of the base member relative to other portions of the respective condyle pad adjustment arm.

23. The system of claim 22, wherein the two condyle pads are configured to be adjustable along a first line perpendicular to the bottom surface the base member and along a second line parallel to the bottom surface of the base member.

24. The system of claim 22, wherein the U-bar assembly further comprises a linear track disposed adjacent to and along the bottom surface, extending between the lateral ends, wherein the patella pad is slidably affixed to the linear track and wherein the linear track is configured to allow the patella pad to move between the lateral ends.

25. The system of claim 21, wherein the patella pad has a contact surface configured to be moved along a line perpendicular to the bottom surface of the base member and selectively locked at various points along the line at various distances away from the bottom surface.

26. The system of claim 20, wherein a diameter of the concave shaped curvature of the thigh cradle narrows diametrically from the proximal end thereof to the distal end thereof.

27. The system of claim 25, wherein the contact surface of the patella pad is at least one of cushioned, deformable, and resilient.

28. The system of claim 15, wherein the linear actuator is affixed to the base between the U-bar assembly and a heel cradle of the heel cradle assembly.

29. The system of claim 15, wherein the heel cradle assembly further comprises an internal-external (IE) rotational fixture mounted on a carriage, and a heel cradle mounted on the IE rotational fixture.

30. The system of claim 29, wherein the carriage has a bottom surface mounted to a first linear track extending in a direction perpendicular to a line extending through the proximal end and distal end of the base to facilitate varus-valgus laxity testing.

31. The system of claim 30, wherein the heel cradle is mounted on the IE rotational fixture via a rotary shaft and further comprising a second linear track affixed to a top surface of the carriage, wherein the top surface of the carriage is opposite the bottom surface and the second linear track is shorter in length than the first linear track and extends in a direction perpendicular to the first linear track and parallel to the line extending through the proximal end and distal end of the base.

\* \* \* \* \*